United States Patent
Lin et al.

(10) Patent No.: US 8,434,701 B2
(45) Date of Patent: May 7, 2013

(54) DEVICE FOR INTERMITTENTLY JETTING GAS

(75) Inventors: Jin Lin, Beijing (CN); Wen He, Beijing (CN); Ping'an Luo, Beijing (CN); Xiaoti Yin, Beijing (CN); Xinmin Liu, Beijing (CN)

(73) Assignee: NucTech Company Limited, Beijing (CN)

( * ) Notice: Subject to any disclaimer, the term of this patent is extended or adjusted under 35 U.S.C. 154(b) by 300 days.

(21) Appl. No.: 12/747,476

(22) PCT Filed: Dec. 23, 2008

(86) PCT No.: PCT/CN2008/002048
§ 371 (c)(1),
(2), (4) Date: Jun. 10, 2010

(87) PCT Pub. No.: WO2009/092190
PCT Pub. Date: Jul. 30, 2009

(65) Prior Publication Data
US 2010/0269930 A1    Oct. 28, 2010

(30) Foreign Application Priority Data
Dec. 27, 2007  (CN) .......................... 2007 1 0304362

(51) Int. Cl.
*B05B 1/26* (2006.01)
(52) U.S. Cl.
USPC .......................................... 239/524; 239/500
(58) Field of Classification Search .................. 239/500, 239/507, 524
See application file for complete search history.

(56) References Cited

U.S. PATENT DOCUMENTS
| | | |
|---|---|---|
| 5,915,268 A | 6/1999 | Linker et al. |
| 6,073,499 A | 6/2000 | Settles |
| 2001/0049926 A1 | 12/2001 | Davies |

FOREIGN PATENT DOCUMENTS
| | | | |
|---|---|---|---|
| CN | 2768876 Y | | 4/2006 |
| CN | 201152835 | | 11/2008 |
| EP | 1286151 A1 | | 2/2003 |
| JP | 60064614 A | | 4/1985 |
| JP | 04032639 | | 2/1992 |
| JP | 6174278 A | | 6/1994 |
| JP | 11344136 A | * | 12/1999 |
| JP | 11344136 A | | 12/1999 |
| JP | 2007263590 A | | 10/2007 |
| JP | 2007263590 A | * | 10/2007 |

OTHER PUBLICATIONS

The German Office Action mailed Jan. 10, 2012 for 11 2008 003 335.8, 8 pages.
International Search Report for Application No. PCT/CN2008/002048, dated Mar. 26, 2009, 7 pgs.

* cited by examiner

*Primary Examiner* — Len Tran
*Assistant Examiner* — Viet Le
(74) *Attorney, Agent, or Firm* — Lee & Hayes, PLLC

(57) ABSTRACT

A device for intermittently jetting gas includes a gas source, a gas conduit with one end being communicated with the gas source and the other end being in communication with a nozzle, a rotary disc and a motor, the disc being mounted on a rotating shaft of the motor for rotating along with the shaft, wherein the rotary disc is provided with at least one opening through which a gas in the gas conduit is jetted when the opening is aligned with the outlet of the gas conduit. The device can freely adjust the gas jetting frequency by adjusting the rotation speed of the motor, and thus increase the gas jetting frequency and effectively flow off the suspicious particles carried in the human clothes.

5 Claims, 1 Drawing Sheet

… (1)

DEVICE FOR INTERMITTENTLY JETTING GAS

CROSS REFERENCE TO RELATED PATENT APPLICATIONS

This application is a national stage application of an international patent application PCT/CN2008/002048, filed Dec. 23, 2008, entitled "An Intermittently Air Jetting Device", which claims priority from Chinese patent application 200710304362.X, filed Dec. 27, 2007, entitled "An Intermittently Air Jetting Device", which applications are hereby incorporated in their entirety by reference.

TECHNICAL FIELD

The present disclosure relates to an apparatus for quickly jetting gas, and in particular, to a device for intermittently jetting gas to blow off suspicious or contraband particles entrapped in human clothes.

DESCRIPTION OF THE RELATED ART

With development of IMS technique, it is possible to detect suspicious particles carried by passengers, such as drugs, explosive, and so on. When the IMS technique is applied to monitor whether the passengers carry drugs, explosive, and so on, an apparatus for quickly jetting gas is first used to blow off the suspicious particles carried by passengers. Then, the particles are sucked into the IMS system to be measured and analyzed. In recent years, experts have studied door-type passenger inspection technique and filed many patent applications, such as EP1286151A1, U.S. Pat. No. 5,915,268A1, U.S. Pat. No. 6,073,499A1, US2001049926A1, etc. In these patent applications, many solutions have been proposed to blow off the suspicious particles carried in human clothes. In U.S. patent application No. US2001049926A1, an apparatus that blows passengers to be inspected using continuous gas flow is disclosed. Afterwards, apparatuses that beat upon clothes using high-pressure gas jetting heads are proposed, and the jetting direction of the gas jetting heads or the flowing direction of the blown gas are continuously varied upwards or downwards. These methods and apparatuses are disclosed in patent applications EP1286151A1, U.S. Pat. No. 5,915,268A1, and U.S. Pat. No. 6,073,499A1, respectively.

In the existing IMS apparatuses that use jetting heads to jet high pressure gas, common solenoid valves are used to control ON and OFF of a gas passage. Because of low response speed of these type of valves with full payload, gas jetting frequency is limited, and it is hard to realize ON and OFF period of less than 80 ms (ON for 40 ms and OFF for 40 ms).

SUMMARY

Accordingly, it is desired to provide a device for intermittently jetting gas with high and adjustable gas jetting frequency.

In order to achieve the above object, the present disclosure provides a device for intermittently jetting gas comprising a gas source and a gas conduit with one end being in communication with the gas source, and the other end being in communication with a nozzle, wherein the device further comprises a rotary disc and a motor, the rotary disc being mounted on a rotating shaft for rotating along with the rotating shaft of the motor, wherein the rotary disc is provided with at least one opening through which gas from the gas conduit is jetted when the opening is aligned with the nozzle.

Compared with the prior art, since the present disclosure employs a disc structure driven by a motor, the device can freely adjust the gas jetting frequency by adjusting the rotation speed of the motor, thereby increasing the gas jetting frequency and effectively blowing off the suspicious particles carried in the human clothes.

BRIEF DESCRIPTION OF THE DRAWINGS

FIG. 1a depicts a schematic structural view of a device for intermittently jetting gas according to the present disclosure;

FIG. 1b depicts a front view of the rotary disc of FIG. 1a;

FIG. 2a depicts a schematic structural view of a device for intermittently jetting gas with a sealing device according to the present disclosure; and FIG. 2b depicts a front view of the rotary disc of FIG. 2a.

DETAILED DESCRIPTION OF THE PREFERRED EMBODIMENTS

The First Embodiment

Figure 1:
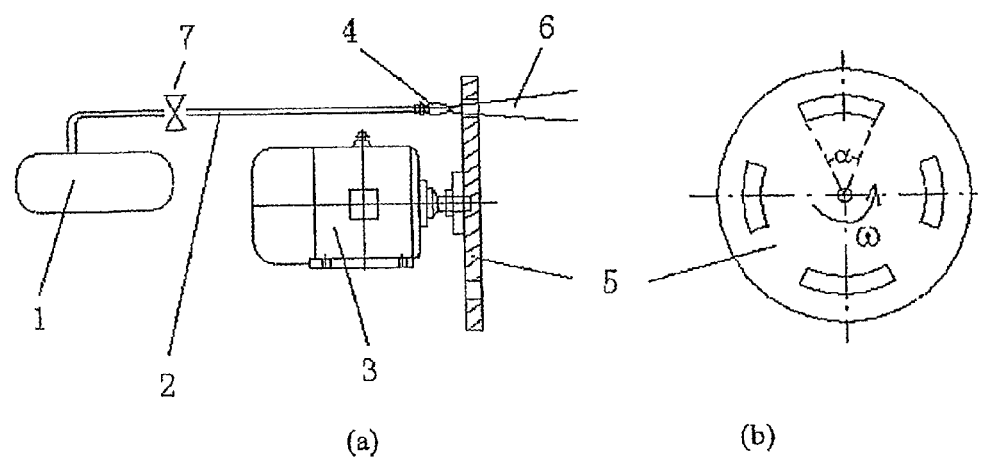

FIGS. 1a and 1b depict schematic structural views of an externally disposed device for intermittently jetting gas according to the first embodiment of the present disclosure.

As shown in FIG. 1a, the externally disposed device for intermittently jetting gas comprises a gas source 1, a gas conduit 2, a rotary disc 5 and a motor 3. One end of the gas conduit 2 is communicated with the gas source 1, and the other end (i.e., an outlet of the gas conduit 2) of the gas conduit 2 is in communication with a nozzle 4 facing a side disc surface of the rotary disc 5. The rotary disc 5 is mounted on a rotating shaft of the motor 3 to rotate along with the rotating shaft of the motor.

Further, the gas conduit 2 is provided with a main switching solenoid valve 7 for gas passage (or may be provided with a pulse control switch).

Further, the gas source may be a gas pump 1 for providing high pressure gas. The pressure of the high pressure gas is generally between 0.2 and 0.8 MPa, preferably about 0.5 MPa. The gas source can be any suitable gas, such as purified air or nitrogen gas.

As shown in FIG. 1b, the rotary disc 5 is provided with four openings. Each opening is in a circular arc shape, and the center of circle of the circular arc shaped openings is coincident with the center of the rotary disc. The four openings in the rotary disc 5 are evenly distributed in the rotary disc 5 at intervals. Further, the width of the openings is designed to allow the gas flow jetted from the nozzle 4 to flow through the openings without any obstruction.

As shown in FIG. 1a, as the rotary disc and the motor are directly exposed to outside and are not sealed by a sealing device, the rotary disc and the motor exposed to outside herein are regarded as an externally disposed rotary disc and an externally disposed motor.

Next, the operation principle of the first embodiment of the present disclosure is explained by reference to FIG. 1a.

As shown in FIG. 1a, the gas pump 1 is first energized and inflated. The solenoid valve 7 is switched to ON. The motor 3 is energized to drive the rotary disc 5 to be rotated. When the openings in the rotary disc 5 are rotated to be aligned with the nozzle 4, the high-pressure gas flow 6 jetted from the nozzle 4 is jetted via the openings in the rotary disc 5. When the openings in the rotary disc 5 are rotated to be misaligned with the nozzle 4, the high-pressure gas flow 6 jetted from the nozzle 4 is blocked by the rotary disc 5 and cannot be jetted via the rotary disc 5. In this way, the high-pressure gas flow 6 jetted from the nozzle 4 is discontinuously blocked by the rotary disc 5, such that a pulsed high-pressure gas flow jetted at a certain frequency is generated. This gas flow beats upon the clothes worn by a passenger, so that the suspicious particles carried on the human bodies can be easily blown off and then be collected, detected and analyzed by a system.

As shown in FIG. 1a, if the rotation speed ω (radian/s) of the motor, the center angle α (degree) corresponding to the circular arc shaped openings, and the number n of the circular arc shaped openings are known, time t1 (s) for each jetting ON and time t2 (s) for each jetting OFF can be calculated by the following equation.

$$t_1 = \frac{\pi\alpha}{180\omega} \quad (1)$$

$$t_2 = \frac{\pi(360 - n\alpha)}{180n\omega} \quad (2)$$

Thus, the period T for each jetting ON and OFF is given by:

$$T = t_1 + t_2 = \frac{\pi\alpha}{180\omega} + \frac{\pi(360 - n\alpha)}{180n\omega} = \frac{2\pi}{n\omega} \quad (3)$$

and the gas jetting frequency f is given by:

$$f = \frac{1}{T} = \frac{n\omega}{2\pi} \quad (4)$$

It can be seen from the above calculation that the gas jetting frequency is related to or dependent upon the rotation speed ω of the motor and the number n of the circular arc shaped openings. Therefore, the gas jetting frequency can be increased by increasing the rotation speed ω of the motor or the number n of the circular arc shaped openings to obtain a high gas jetting frequency.

Compared with the prior art, the device according to the present disclosure can freely adjust jetting interval of a jetting head, eliminate influence of the response time of the common solenoid valve on the gas jetting frequency, increase the jetting frequency of the system, and improve efficiency of blowing off suspicious particles carried in human clothes. Since the present disclosure employs a mechanical rotary mechanism, reliability is improved, and a defect that a common solenoid valve is prone to be damaged due to repeated engagement and disengagement is overcome, thereby reducing failure and malfunction of the whole system.

The Second Embodiment

Figure 2:
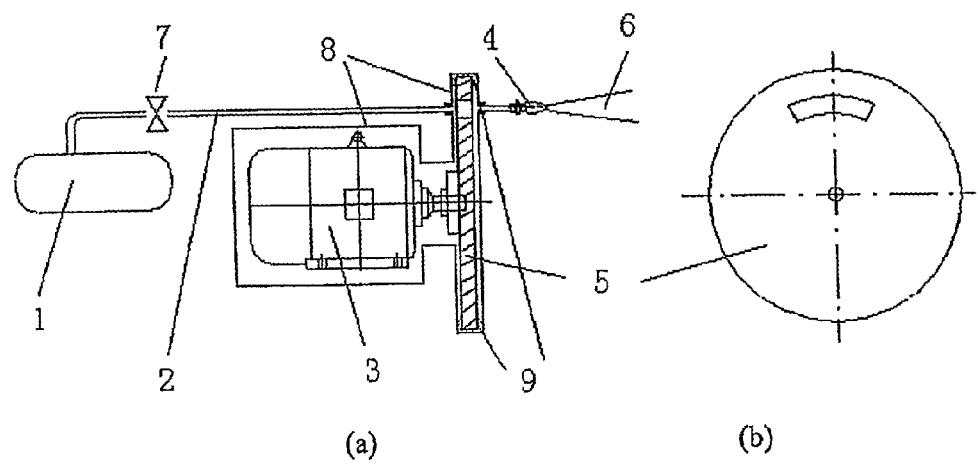

FIGS. 2a and 2b depict schematic structural views of an internally disposed device for intermittently jetting gas according to the second embodiment of the present disclosure.

As shown in FIG. 2a, the internally disposed device for intermittently jetting gas comprises a gas source 1, a gas conduit 2, a rotary disc 5, a motor 3 and a sealing device 9. One end of the gas conduit 2 is communicated with the gas source 1, and the other end (i.e., an outlet of the gas conduit 2) of the gas conduit 2 is communicated with a side housing 8 of the sealing device 9. A nozzle 4 is mounted on another side housing 8 of the sealing device 9 opposite to the outlet of the gas conduit 2. The rotary disc 5 is mounted on a rotating shaft of the motor 3 to rotate along with the rotating shaft of the motor. Both the rotary disc 5 and the motor 3 are provided within the sealing device 9.

Further, the gas conduit 2 is provided with a main switching solenoid valve 7 for gas passage (or may be provided with a pulse controlled switch).

Further, the gas source may be a gas pump 1 for providing high-pressure gas. The pressure of the high pressure gas is generally between 0.2 and 0.8 MPa, preferably is about 0.5 MPa.

As shown in FIG. 2b, the rotary disc 5 is provided with a circular arc shaped opening. The center of circle of the circular arc shaped opening is coincident with the center of the rotary disc. Further, the width of the opening is designed to allow the gas flow jetted from the outlet of the gas conduit 2 to flow through the opening without any obstruction.

As shown in FIG. 2a, as the rotary disc and the motor are disposed within the sealing device, the rotary disc and the motor hermetically arranged herein are regarded as an internally disposed rotary disc and an internally disposed motor.

Next, the operation principle of the second embodiment of the present disclosure is explained by reference to FIG. 2a.

As shown in FIG. 2a, the gas pump 1 is first energized and inflated. The solenoid valve 7 is switched to ON. If the motor 3 is not energized, the rotary disc 5 is not rotated. In this case, after a certain time, the nozzle 4 will jet the high-pressure gas flow 6 with high balance gas pressure $P_0$, no matter whether the opening in the rotary disc 5 is aligned with the nozzle 4.

If the motor 3 is energized to drive the rotary disc 5 to be rotated, when the opening in the rotary disc 5 is rotated to be aligned with the outlet of the gas conduit 2 (or the nozzle 4), the nozzle 4 jets the gas having a first pressure $P_{max}(t)$. When the opening in the rotary disc 5 is rotated to be misaligned with the outlet of the gas conduit 2 (or the nozzle 4), the high gas pressure gas flow jetted from the outlet of the gas conduit 2 will be blocked by the rotary disc 5 and cannot be directly jetted from the nozzle 4. However, since the rotary disc 5 is sealed within the sealing device and divides the internal space of the sealing device into a left space and a right space which are communicated with each other via the opening in the rotary disc 5, the high pressure gas flow in the left space can still flow into the right space via the opening and be jetted from the nozzle 4, but the pressure (a second gas pressure $P_{min}(t)$) of the gas jetted from the nozzle 4 is less than the first pressure $P_{max}(t)$ due to disturbance of the high-speed rotating rotary disc 5 to the gas flow. Based on the disturbance theory, there is the following relationship: $0<P_{min}(t)<P_0<P_{max}(t)$. If duration time t for gas jetting is too long, $P_{min}(t)$ and $P_{max}(t)$ may be caused to approximate to each other. At this time, the solenoid valve 7 can be controlled to be OFF, and the status of the device is reset. Then, the solenoid valve 7 is switched to ON again, and the status of the device enters the next disturbance cycle. The sealing device 9 is designed for separating the gas flows distributed on the two sides of the rotary disc respectively. The sealing device 9 functions to enhance pressure difference between $P_{min}(t)$ and $P_{max}(t)$.

In this way, the gas flow is jetted with a certain frequency to beat upon the clothes worn by a passenger, so that the suspicious particles carried on the human bodies can be easily blown off and then be collected, detected and analyzed by the system.

Other Possible Modifications

The number of the openings in the rotary disc in the above-mentioned embodiments may be of any suitable number, such as 2, 3, 5 or more.

In the second embodiment, both the motor and the rotary disc are provided within the sealing device. Alternatively, only the rotary disc is provided within the sealing device.

By reading the description, these simple replacement and modification are obvious to one skilled in the art and will not be described herein.

While the embodiments of the present disclosure have been shown and described, it will be appreciated by one skilled in the art that modifications may be made to the embodiments as described without departing from the scope of the claims set out below.

What is claimed is:

1. A device for intermittently jetting gas, comprising:
   a gas source;
   a nozzle;
   a gas conduit with a first end in communication with the gas source and a second end being in communication with the nozzle;
   a rotary disc; and
   a motor having a shaft, said rotary disc being mounted on the shaft of the motor for rotating along with the shaft of the motor, said rotary disc having at least one opening through which a gas in the gas conduit can be jetted from the nozzle when the at least one opening is aligned with the nozzle,
   wherein said rotary disc and said motor are internally disposed;
   said rotary disc and said motor are received within a sealing device;
   said rotary disc divides an internal space of the sealing device into a left space and a right space which are communicated with each other via the at least one opening in the rotary disc;
   an outlet of the gas conduit is communicated with a side of the sealing device, and the nozzle is mounted on another side of the sealing device;
   when the nozzle is aligned with the at least one opening of the rotary disc, a gas with a first pressure is jetted from the nozzle; and
   when the nozzle is misaligned with the at least one opening of the rotary disc, a gas, having a second pressure different from the first pressure, is jetted from the nozzle.

2. The device for intermittently jetting gas according to claim 1, wherein said at least one opening is a circular arc shaped opening, and wherein a center of circle of the circular arc shaped opening is coincident with a center of the rotary disc.

3. The device for intermittently jetting gas according to claim 1, wherein said rotary disc is provided with one opening.

4. The device for intermittently jetting gas according to claim 1, wherein said rotary disc is provided with more than two openings, and wherein the more than two openings are evenly distributed at intervals.

5. The device for intermittently jetting gas according to claim 1, wherein said gas conduit is provided with a switching solenoid valve or a pulse controlled switch to control gas passage.

* * * * *